(12) United States Patent
Hong et al.

(10) Patent No.: US 6,866,805 B2
(45) Date of Patent: Mar. 15, 2005

(54) HYBRID INTRAVASCULAR STENT

(75) Inventors: James Hong, San Jose, CA (US); Rahul Bhagat, San Jose, CA (US); Syed Hossainy, Fremont, CA (US); Santosh Prabhu, San Jose, CA (US); K.T. Venkateswara Rao, San Jose, CA (US); Ashok Shah, San Jose, CA (US); Srinivasan Sridharan, Morgan Hill, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 223 days.

(21) Appl. No.: 10/033,380

(22) Filed: Dec. 27, 2001

(65) Prior Publication Data

US 2004/0199242 A1 Oct. 7, 2004

(51) Int. Cl.7 .......................... B29C 45/14; B29C 70/70
(52) U.S. Cl. .................... 264/161; 264/230; 264/271.1; 264/278; 264/279.1; 264/305; 264/306; 623/901
(58) Field of Search ................................. 264/230, 250, 264/254, 259, 271.1, 261, 263, 277, 279, 279.1, 301, 304, 305, 308, 161, 275, 278, 306; 623/1.11, 1.12, 1.13, 1.42–1.46, 901

(56) References Cited

U.S. PATENT DOCUMENTS

| 5,123,917 A | 6/1992 | Lee |
| 5,593,417 A | 1/1997 | Rhodes |
| 5,837,313 A | 11/1998 | Ding et al. |
| 6,004,348 A | 12/1999 | Banas et al. |
| 6,013,854 A | 1/2000 | Moriuchi |
| 6,156,064 A | 12/2000 | Chouinard |
| 6,179,817 B1 | 1/2001 | Zhong |
| 6,245,099 B1 | 6/2001 | Edwin et al. |
| 6,251,136 B1 | 6/2001 | Guruwaiya et al. |
| 2001/0025130 A1 | 9/2001 | Tomonto |

FOREIGN PATENT DOCUMENTS

| EP | 0 931 520 A2 | 7/1999 |
| WO | WO 98/20810 | 5/1998 |
| WO | WO 01/01888 A1 | 1/2001 |
| WO | WO 01/21101 A1 | 3/2001 |
| WO | WO 01/82835 A2 | 11/2001 |
| WO | WO 02/053066 A1 | 7/2002 |

*Primary Examiner*—Angela Ortiz
(74) *Attorney, Agent, or Firm*—Fulwider Patton Lee & Utecht, LLP

(57) ABSTRACT

A hybrid stent is formed which exhibits both high flexibility and high radial strength. The expandable hybrid stent for implantation in a body lumen, such as a coronary artery, consists of radially expandable cylindrical rings generally aligned on a common longitudinal axis and interconnected by one or more links. In one embodiment, a dip-coated covered stent is formed by encapsulating cylindrical rings within a polymer material. In other embodiments, at least some of the rings and links are formed of a polymer material which provides longitudinal and flexural flexibility to the stent. These polymer rings and links are alternated with metallic rings and links in various configurations to attain sufficient column strength along with the requisite flexibility in holding open the target site within the body lumen. Alternatively, a laminated, linkless hybrid stent is formed by encapsulating cylindrical rings within a polymer tube.

23 Claims, 8 Drawing Sheets

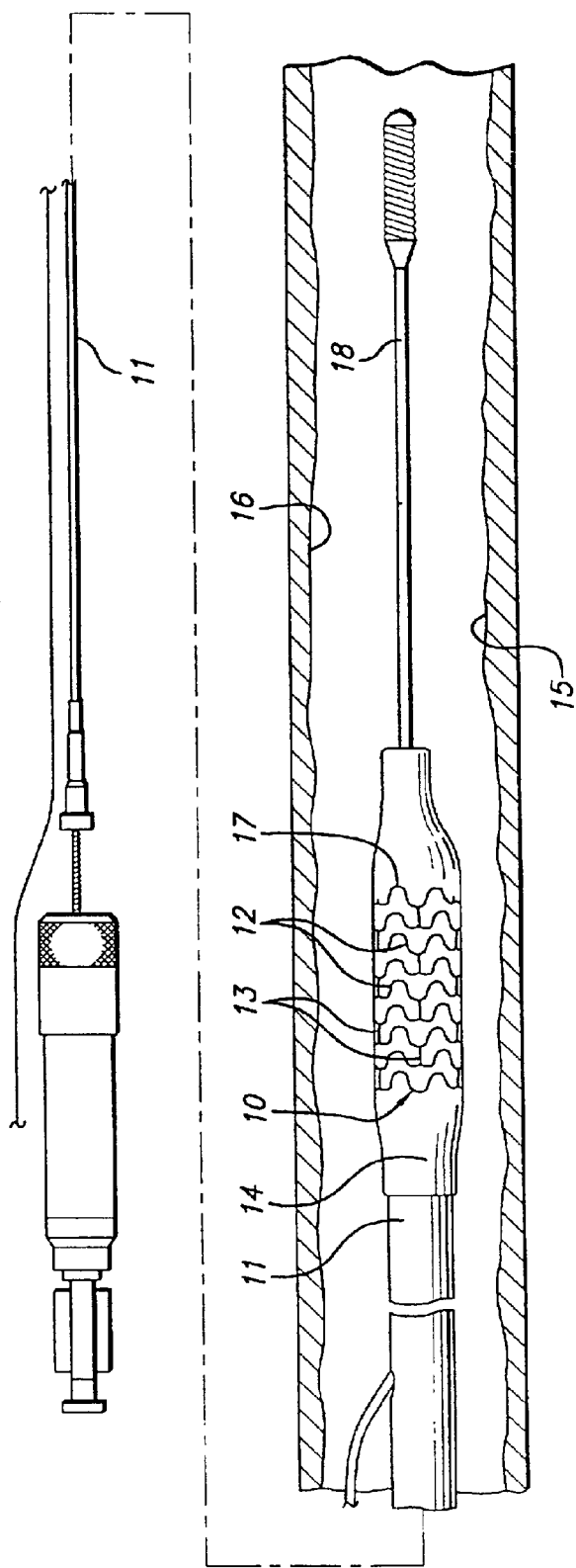
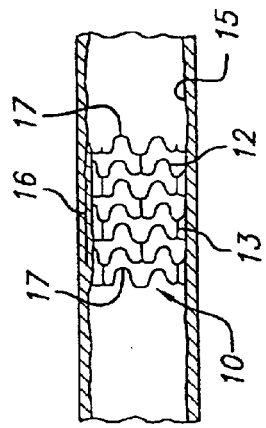
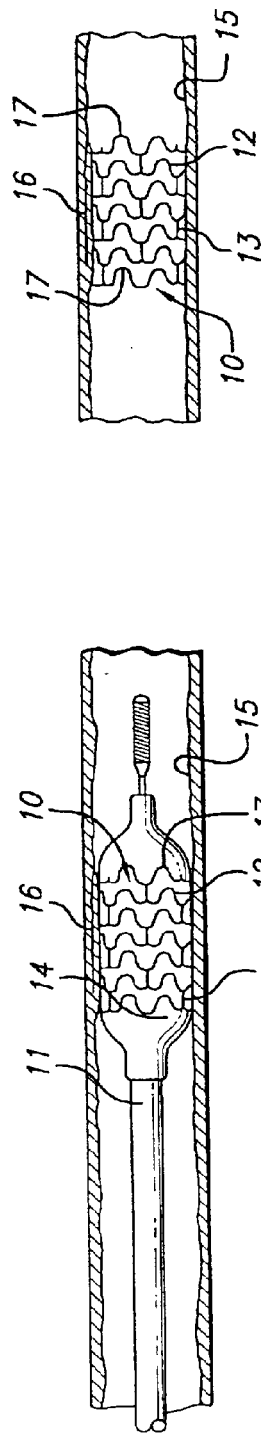

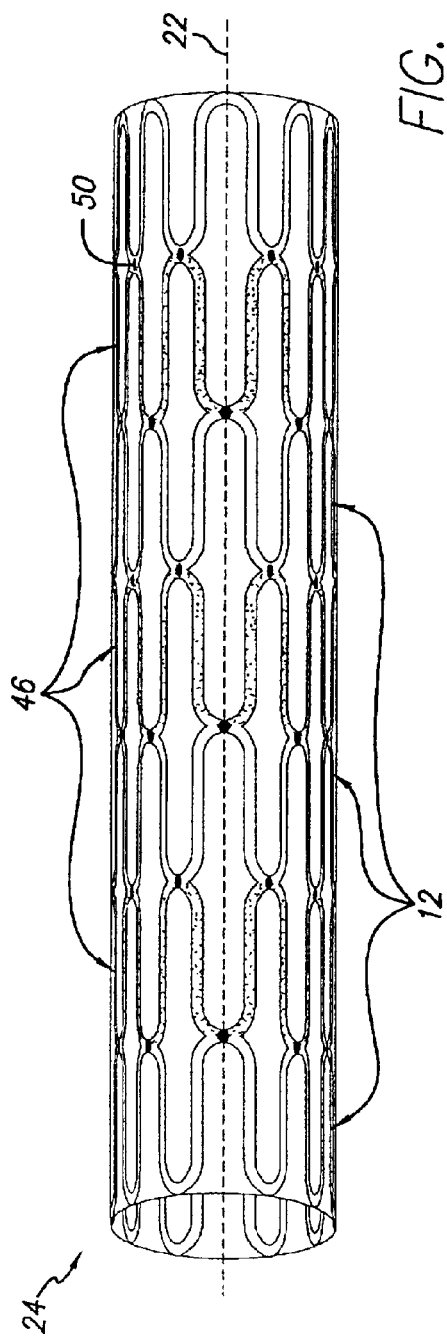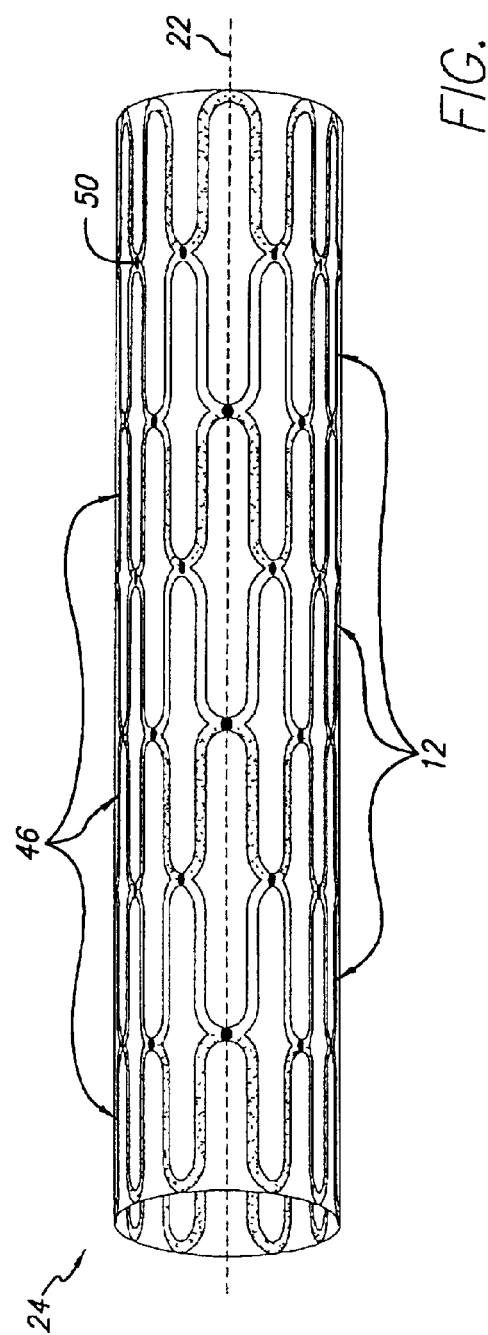

HYBRID INTRAVASCULAR STENT

BACKGROUND OF THE INVENTION

This invention relates to expandable endoprosthesis devices, generally called stents, which are adapted to be implanted into a patient's body lumen, such as a blood vessel, to maintain the patency thereof. These devices are useful in the treatment of atherosclerotic stenosis in blood vessels.

Stents are generally tubular-shaped devices which function to hold open a segment of a blood vessel, coronary artery, or other anatomical lumen. They are particularly suitable for use to support and hold back a dissected arterial lining which can occlude the fluid passageway therethrough.

Various means have been described to deliver and implant stents. One method frequently described for delivering a stent to a desired intraluminal location includes mounting the expandable stent on an expandable member, such as a balloon provided on the distal end of an intravascular catheter, advancing the catheter to the desired location within the patient's body lumen, inflating the balloon on the catheter to expand the stent into a permanent expanded condition and then deflating the balloon and removing the catheter. One of the difficulties encountered using prior stents involved maintaining the radial rigidity needed to hold open a body lumen while at the same time maintaining the longitudinal flexibility of the stent to facilitate its delivery. Once the stent is mounted on the balloon portion of the catheter, it is often delivered through tortuous vessels, including tortuous coronary arteries. The stent must have numerous properties and characteristics, including a high degree of flexibility in order to appropriately navigate the tortuous coronary arteries. This flexibility must be balanced against other features including radial strength once the stent has been expanded and implanted in the artery. While other numerous prior art stents have had sufficient radial strength to hold open and maintain the patency of a coronary artery, they have lacked the flexibility required to easily navigate tortuous vessels without damaging the vessels during delivery.

Generally speaking, most prior art intravascular stents are formed from a metal such as stainless steel, which is balloon expandable and plastically deforms upon expansion to hold open a vessel. The component parts of these types of stents typically are all formed of the same type of metal, i.e., stainless steel. Other types of prior art stents may be formed from a polymer, again all of the component parts being formed from the same polymer material. These types of stents, the ones formed from a metal and the ones formed from a polymer, each have advantages and disadvantages. One of the advantages of the metallic stents is their high radial strength once expanded and implanted in the vessel. A disadvantage may be that the metallic stent lacks flexibility which is important during the delivery of the stent to the target site. With respect to polymer stents, they may have a tendency to be quite flexible and are advantageous for use during delivery through tortuous vessels, however, such polymer stents may lack the radial strength necessary to adequately support the lumen once implanted.

What has been needed and heretofore unavailable is a method of making a hybrid stent which has a high degree of flexibility so that it can be advanced through tortuous passageways and can be readily expanded and yet have the mechanical strength to hold open the body lumen into which it is expanded. The present invention satisfies this need and others.

SUMMARY OF THE INVENTION

The present invention is directed to methods of making an intravascular hybrid stent which is highly flexible along its longitudinal axis to facilitate delivery through tortuous body lumens but which is also strong and stable enough radially in its expanded condition to maintain the patency of a body lumen when implanted therein. One embodiment of the present invention involves a method of making a dip-coated covered stent for use in a body lumen. The dip-coated covered stent is formed by encapsulating equally spaced cylindrical stent rings with a biocompatible polymer while on a mandrel assembly through a dip-coating process. Once the desired thickness of the coating is achieved, the polymer cures thereon and the covered stent is removed from the mandrel assembly. If side branch access is desired, a perforated pattern can be cut into the dip-coated stent to produce the final configuration. A number of metallic materials may be used for the cylindrical rings, such as stainless steel, titanium, nickel titanium, tantalum, gold, cobalt-chromium, platinum, palladium, and iradium. Likewise, a number of various biocompatible polymers may be used to coat the metallic cylindrical rings and form the stent.

In another embodiment of the present invention, a method of making a hybrid stent having alternating rings and links formed of a biocompatible polymer material for use in a body lumen is disclosed. This hybrid approach creates a stent that exhibits the desirable characteristics of high flexibility and high radial strength. The flexibility of the stainless steel stent is increased by incorporating the mechanical advantages of polymers (i.e., lower stress, higher strain) to form alternating rings of polymers and connector links along the length of the stent for a more flexible stent system.

In yet another embodiment of the present invention, a linkless hybrid stent is fabricated with alternating cylindrical rings of a polymer material in which adjacent cylindrical rings are directly attached to each other at the peaks, such as by welding. The alternating polymer cylindrical rings can be selectively placed at the stent ends to prevent vessel wall injury at the edges of the stent.

In a further embodiment of the present invention, a laminated, linkless polymer stent is fabricated by laminating a plurality of cylindrical stent rings between two polymer tubes. The lamination of the rings can be performed in accordance with techniques known in the art, such as laser bonding and blow molding. The presence of the polymer tube provides support to an increased portion of the arterial wall thereby increasing the stent scaffolding. The radiopacity of the stent can be increased using metals such as gold, paladium, platinum, and iradium. Further, the stent can be made MRI-compatible by using gold or silver in place of stainless steel.

Each of the embodiments of the present invention set forth above may be further enhanced with the incorporation of drugs into the polymer material to be eluted therefrom in the treatment of disease.

One preferred structure for the expandable cylindrical rings which form the stent of the present invention is generally a circumferential undulating pattern, e.g., serpentine. The open reticulated structure of the stent allows for the perfusion of blood over a large portion of the arterial wall which can improve the healing and repair of a damaged arterial lining.

The stent embodying features of the invention can be readily delivered to the desired body lumen, such as a coronary artery (peripheral vessels, bile ducts, etc.), by mounting the stent on an expandable member of a delivery catheter, for example a balloon, and advancing the catheter and stent assembly through the body lumen to the target site. Generally, the stent is compressed or crimped onto the balloon portion of the catheter so that the stent does not move longitudinally relative to the balloon portion of the catheter during delivery through the arteries, and during expansion of the stent at the target site.

When the stent is expanded, the radial expansion of the expandable cylindrical rings deforms the undulating or serpentine pattern similar to changes in a waveform which result from decreasing the waveform's amplitude and the frequency. The undulating patterns of the individual cylindrical rings can be in phase with each other or out of phase, depending on the stent design. The cylindrical rings of the stent are plastically deformed when expanded so that the stent will remain in the expanded condition and therefore they must be sufficiently rigid when expanded to prevent the collapse thereof in use. During expansion of the stent, portions of the undulating pattern tip outwardly resulting in projecting members on the outer surface of the expanded stent. These projecting members tip radially outwardly from the outer surface of the stent and embed into the vessel wall and help secure the expanded stent so that it does not move once it is implanted.

The links which interconnect adjacent cylindrical rings may have a transverse cross-section similar to the transverse dimensions of the undulating components of the expandable cylindrical rings. In one embodiment, all of the links are joined at either the peaks or the valleys of the undulating structure of the cylindrical rings. In this manner, there is little or no shortening of the stent upon expansion.

The number and location of links connecting the rings can be varied in order to vary the desired longitudinal and flexural flexibility in the stent structure both in the unexpanded as well as the expanded condition. These properties are important to minimize alteration of the natural physiology of the body lumen into which the stent is implanted and to maintain the compliance of the body lumen which is internally supported by the stent. Generally, the greater the longitudinal and flexural flexibility of the stent, the easier and the more safely it can be delivered to the target site.

Other features and advantages will become apparent from the following detailed description, taken in conjunction with the accompanying drawings, which illustrate, by way of example, the features of the invention.

BRIEF DESCRIPTION OF THE DRAWINGS

FIG. 1 is an elevational view, partially in section, of a stent embodying features of the invention which is mounted on a delivery catheter and disposed within a damaged artery.

FIG. 2 is an elevational view, partially in section, similar to that shown in FIG. 1 wherein the stent is expanded within a damaged artery.

FIG. 3 is an elevational view, partially in section, depicting the expanded stent within the artery after withdrawal of the delivery catheter.

FIG. 10 is a perspective view of an alternative embodiment of a linkless hybrid stent depicting adjacent cylindrical rings directly attached to each other by welding.

FIG. 11 is a perspective view of an alternative embodiment of a linkless hybrid stent depicting each end of the stent fabricated from a polymer material.

DETAILED DESCRIPTION OF THE PREFERRED EMBODIMENTS

Figure 4:
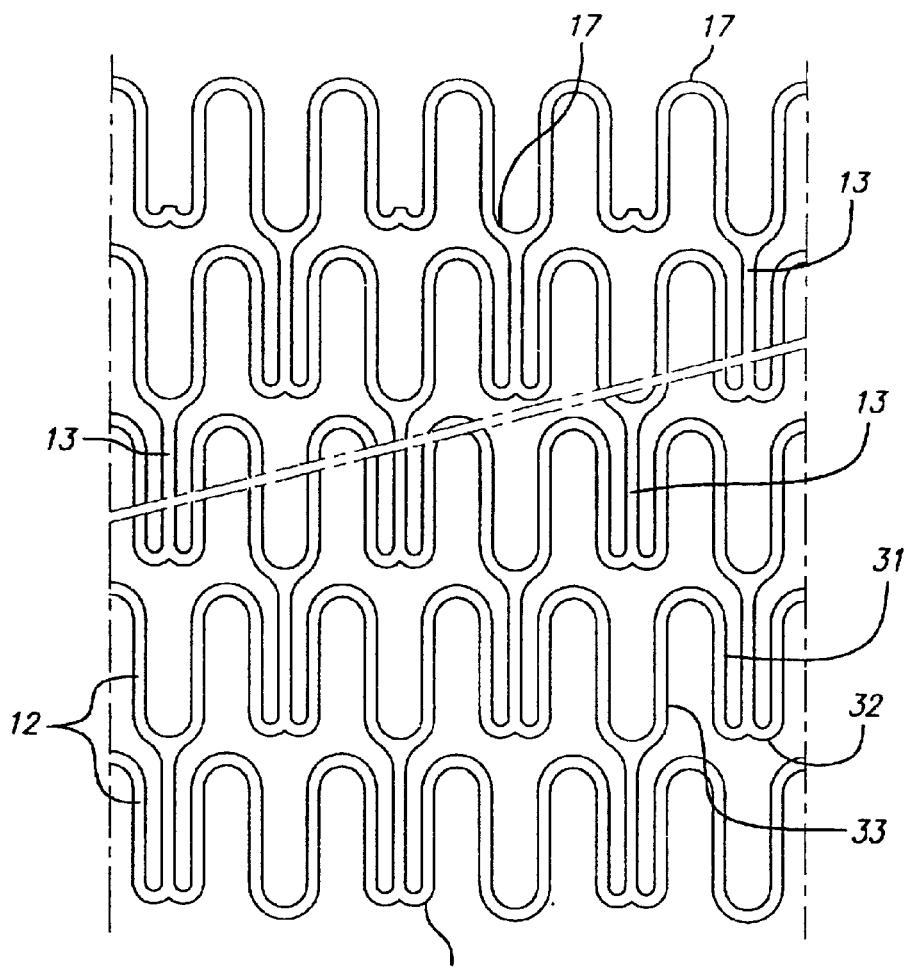
FIG. 4 is a plan view of a flattened section of the stent of the invention, illustrating the cylindrical rings attached by the links.

FIG. 1 illustrates a stent 10 incorporating features of the invention which is mounted onto a delivery catheter 11. The stent generally comprises a plurality of radially expandable cylindrical rings 12 disposed generally coaxially and interconnected by links 13 disposed between adjacent cylindrical elements. The delivery catheter 11 has an expandable portion or balloon 14 for expansion of the stent 10 within an artery 15. The artery 15, as shown in FIG. 1, has an occluded portion of the arterial passageway that has been opened by a previous procedure, such as angioplasty.

The delivery catheter 11 onto which the stent 10 is mounted, is essentially the same as a conventional balloon dilatation catheter for angioplasty procedures. The balloon 14 may be formed of suitable materials such as polyethylene, polyethylene terephthalate, polyvinyl chloride, nylon and ionomers such as Surlyn® manufactured by the Polymer Products Division of the Du Pont Company. Other polymers may also be used. In order for the stent 10 to remain in place on the balloon 14 during delivery to the site of the damage within the artery 15, the stent 10 is crimped or compressed onto the balloon in a known manner.

Each radially expandable cylindrical ring 12 of the stent 10 may be substantially independently expanded to some degree relative to adjacent rings. Therefore, the balloon 14 may be provided with an inflated shape other than cylindrical, e.g., tapered, to facilitate implantation of the stent in a variety of body lumen shapes. Thus, the stent also would have a tapered shape.

In one embodiment, the delivery of the stent 10 is accomplished in the following manner. The stent is first mounted onto the inflatable balloon 14 on the distal extremity of the delivery catheter by crimping or compressing the stent in a known manner. The catheter-stent assembly is introduced within the patient's vasculature in a conventional Seldinger technique through a guiding catheter (not shown). A guide wire 18 is disposed across the damaged arterial section and then the catheter-stent assembly is advanced over a guide wire 18 within the artery 15 until the stent is positioned at the target site 16. The balloon of the catheter is expanded, expanding the stent against the artery, which is illustrated in FIG. 2. While not shown in the drawing, the artery is preferably expanded slightly by the expansion of the stent to seat or otherwise fix the stent to prevent movement. In some circumstances during the treatment of stenotic portions of an artery, the artery may have to be expanded considerably in order to facilitate passage of blood or other fluid therethrough.

The stent 10 serves to hold open the artery 15 after the catheter 11 is withdrawn, as illustrated by FIG. 3. Due to the formation of the stent from an elongated tubular member or a flat sheet, the undulating component of the cylindrical rings 12 of the stent is relatively flat in transverse cross-section, so that when the stent is expanded, the cylindrical rings are pressed into the wall of the artery and as a result do not interfere with the blood flow through the artery. The cylindrical elements 12 of the stent which are pressed into the wall of the artery will eventually be covered with endothelial cell growth which further minimizes blood flow interference. The undulating portion 17 of the cylindrical rings provide good tacking characteristics to prevent stent movement within the artery. Furthermore, the closely spaced cylindrical rings at regular intervals provide uniform support for the wall of the artery 15, and consequently are well adapted to tack up and hold in place small flaps or dissections in the wall of the artery 15.

Although not shown in the drawings, in addition to the balloon-expandable version, the hybrid stent of the present invention may also be made self-expanding with nickel-titanium and deployed by constraining the device inside a sheath.

FIG. 4 is an enlarged plan view of the stent 10 shown in FIG. 1 with one end of the stent shown in an exploded view to illustrate in greater detail the placement of links 13 between adjacent radially expandable cylindrical rings 12. Each of the links on one side of a cylindrical ring is preferably placed to achieve maximum flexibility for a stent. In the embodiment shown in FIG. 4, the stent 10 has three links 13 between adjacent radially expandable cylindrical elements 12, which are spaced 120° apart. Each of the links on one side of a cylindrical ring are offset radially 60° from a corresponding link on the other side of the ring. The alternating link pattern results in a stent having longitudinal and flexural flexibility in essentially all directions due to the placement of the links. Various configurations for the placement of the links are possible, and two examples are illustrated schematically in FIGS. 4–5. However, as previously mentioned, all of the links of an individual stent should be secured to either the peaks or valleys of the undulating structural portions 17 in order to help prevent shortening of the stent during the expansion thereof.

FIG. 4 illustrates a stent of the present invention wherein three links 13 are disposed between radially expandable cylindrical rings 12. The links are distributed around the circumference of the stent at a 120° spacing. Disposing four or more links between adjacent cylindrical rings will generally give rise to the same considerations discussed above for placement of one, two, and three links.

Figure 5:
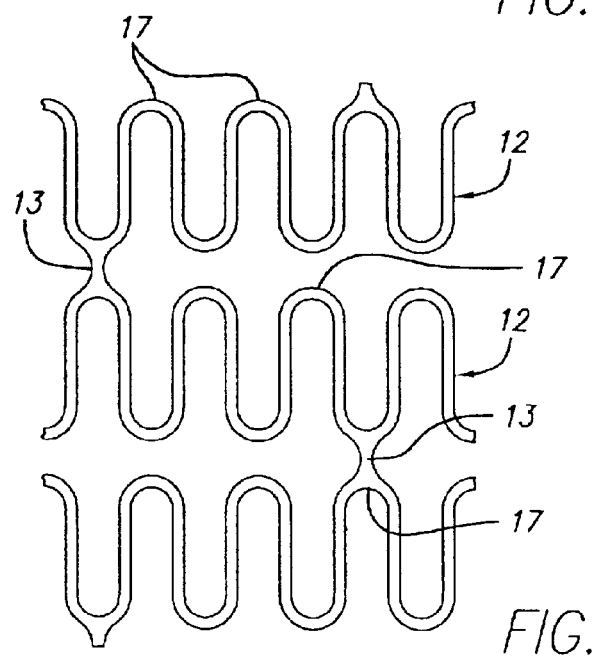
FIG. 5 is a plan view of a flattened section of a stent illustrating an undulating pattern in the expandable cylindrical rings of the stent which are out of phase.

The properties of the stent 10 may also be varied by alteration of the undulating portions 17 of the cylindrical rings 12. FIG. 5 illustrates an alternative stent structure in which the cylindrical rings have an undulating shape so the undulations of one cylindrical ring 12 is out of phase with adjacent cylindrical rings. The particular pattern and how many undulations per unit of length around the circumference of the cylindrical rings, or the amplitude of the undulations, are chosen to fill particular mechanical requirements for the stent, such as radial stiffness.

Figure 6:
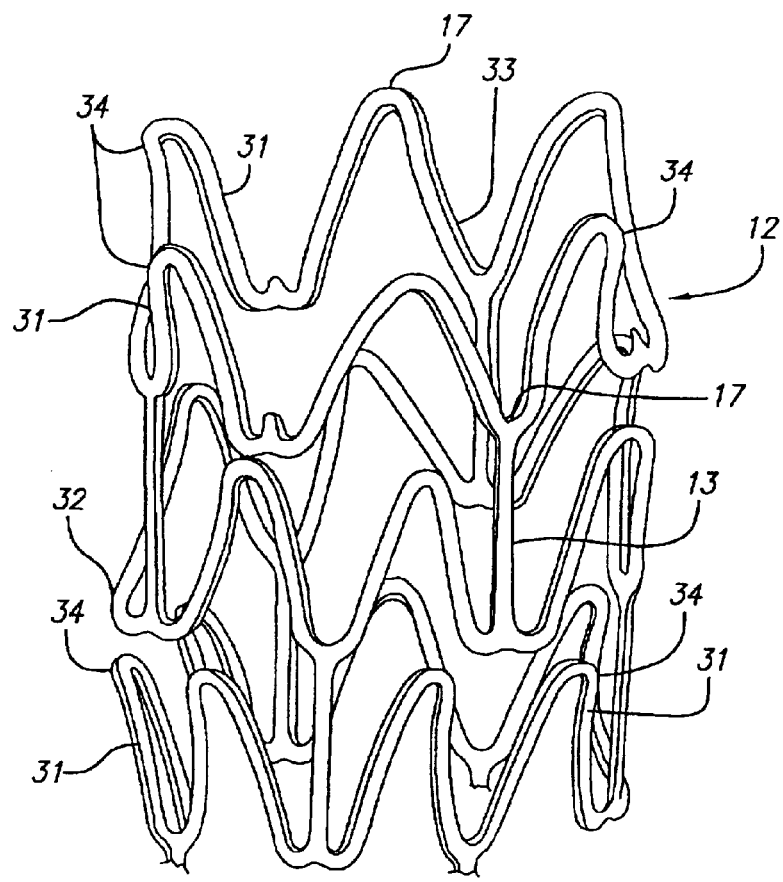
FIG. 6 is a perspective view of the stent of FIG. 4 after it is fully expanded depicting some portions of the stent projecting radially outwardly.

With reference to FIG. 6, the cylindrical rings 12 are in the form of undulating portions 17, as previously mentioned. The undulating portion is made up of a plurality of U-shaped members 31, W-shaped members 32, and Y-shaped members 33, each having a radius that more evenly distributes expansion forces over the various members. After the cylindrical rings 12 have been radially expanded, outwardly projecting edges 34 are formed. That is, during radial expansion some of the U-shaped, W-shaped, or Y-shaped portions may tip radially outwardly thereby forming outwardly projecting edges. These outwardly projecting edges provide for a roughened outer wall surface of the stent 10 and assist in implanting the stent in the vascular wall by embedding into the vascular wall. In other words, outwardly projecting edges embed into the vascular wall, for example artery 15, as depicted in FIG. 3. Depending upon the dimensions of stent 10 and the thickness of the various members making up the serpentine pattern, any of the U-shaped members 31, W-shaped members 32, and Y-shaped members 33 can tip radially outwardly to form a projecting edge 34.

The stent patterns shown in FIGS. 1–6 are for illustration purposes only and can vary in shape and size to accommodate different vessels or body lumens. Thus, rings connected by links can have any structural shapes and are not limited to the aforedescribed undulating rings, U-shaped, W-shaped, and Y-shaped portions, or to straight links connecting the rings.

Figure 12A:
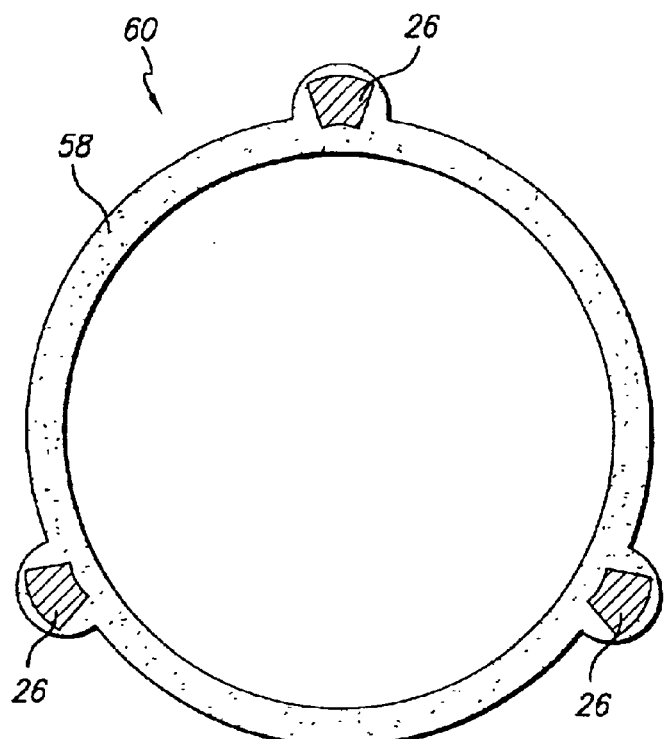
FIG. 12A is a cross-sectional view of a laminated, linkless polymer stent in an alternative embodiment of the invention.
Figure 12B:
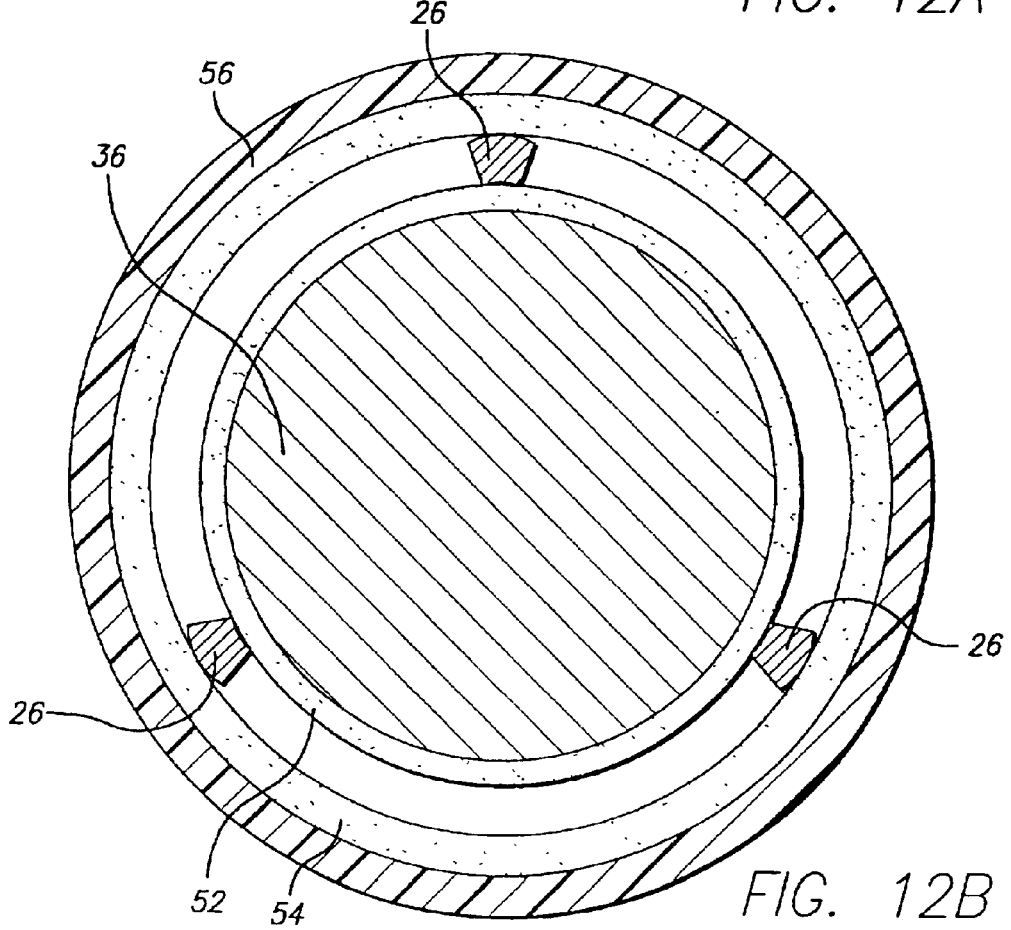
FIG. 12B is a cross-sectional view of each layer that is used in the fabrication of the laminated, linkless polymer stent.
Figure 13:
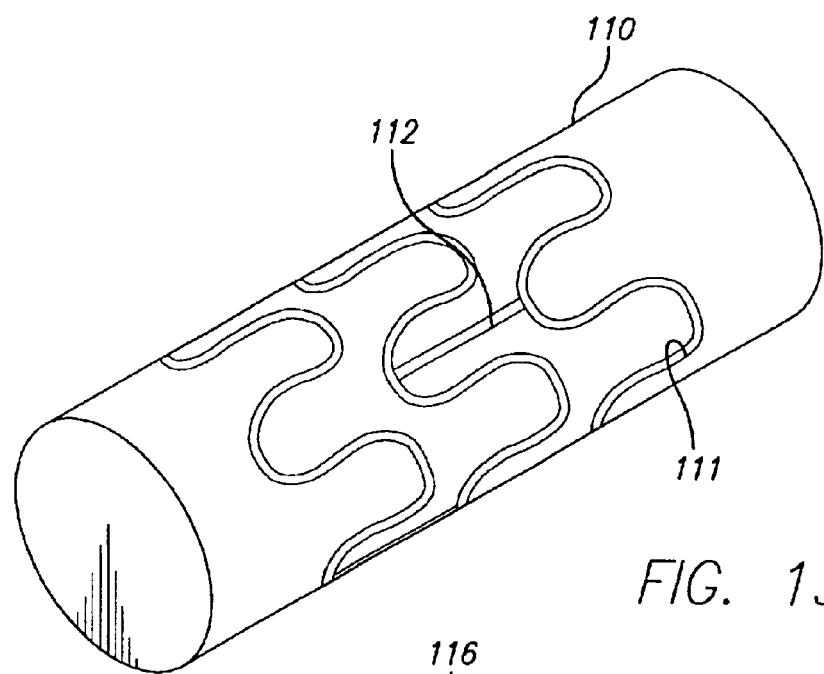
FIG. 13 is a perspective view of a mandrel having grooves for both the cylindrical rings and the links for use in the injection molding process.

In keeping with the invention, the links 13 are formed from a flexible polymer material, or similar material, that is bendable and flexible to enhance longitudinal and flexural flexibility of the stent 10. Additionally, a select number of alternating cylindrical rings 12 of the hybrid stents (FIGS. 8–11) are formed of a polymer material which provide scaffolding, increased flexibility and a reduction in the MRI-imaging artifact as a result of the nonconductive properties of the polymer. In an alternative embodiment described in detail below (FIG. 9), the links 13 are formed of alternating flexible polymer materials and metallic materials. Since the cylindrical rings 12 are independently formed out of a metal, such as stainless steel or the like, the rings must be connected together by the links 13. However, in one particular embodiment (FIG. 10), there are no links 13 connecting the cylindrical rings 12. Rather, adjacent cylindrical rings 12 are directly attached to one another, such as by welding, or other similar means. Alternatively, the stent can be a laminated, linkless polymeric stent as depicted in FIGS. 12A–12B. A primary aspect of the invention includes various methods for making hybrid stents having an alternating pattern of cylindrical rings 12 and links 13 using biocompatible polymer materials and metallic materials in order to achieve the desired combination of high flexibility while exhibiting high radial strength. More particularly, the hybrid stent configuration of the present invention provides a new way to impart radial strength to a polymer stent, and/or a biodegradable stent by having reinforcement through the addition of metal rings in between.

Figure 7A:
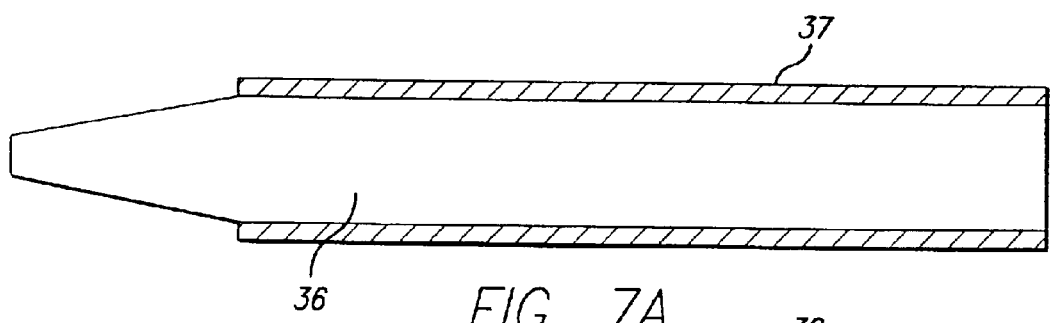
FIG. 7A is a plan view of a mandrel with a base coat thereon used in forming a dip-coated covered stent of the invention.
Figure 7B:
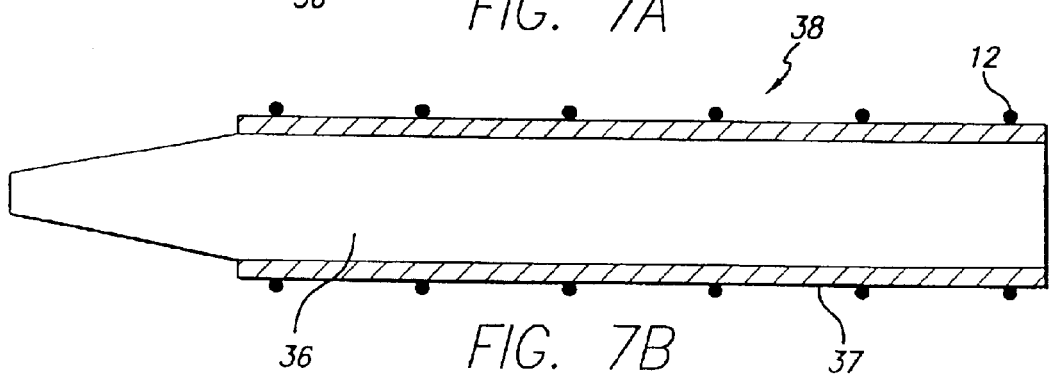
FIG. 7B is a plan view of a mandrel assembly with a plurality of cylindrical stent rings mounted thereon used in forming the dip-coated covered stent of the invention.
Figure 7C:
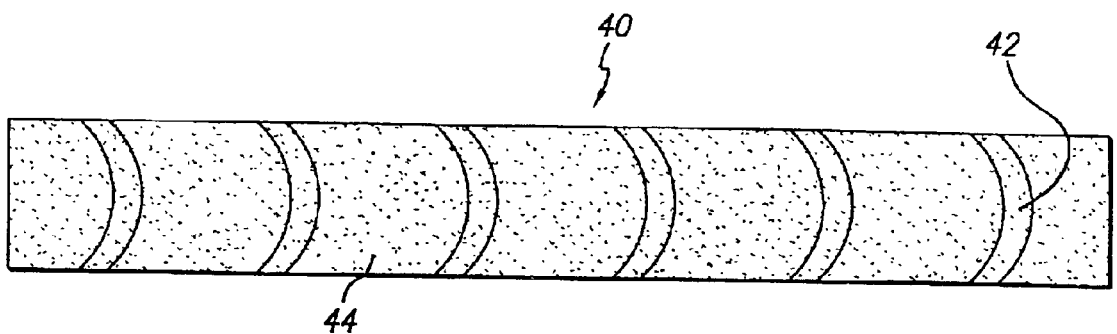
FIG. 7C is a plan view of the newly fabricated dip-coated covered stent without side branch access.

FIGS. 7A–7C illustrates a method of making a dip-coated covered stent in accordance with the invention without side branch access. A mandrel 36 fabricated from a teflon (PTFE) material is initially coated with a biocompatible polymer material to form a base coat 37 thereon, as shown in FIG. 7A. The mandrel can be made from any material (e.g., metal or plastic) that is compatible with the dip-coating process described herein. However, it is preferable that the mandrel is made from a polymer such as ePTFE because the mandrel can be removed by "necking" in order to release the coated polymer stent. Additional inert materials from which the mandrel may be formed include polyimide, polyethylene, PET, and nylon. Once the polymer has cured thereon, a plurality of cylindrical stent rings 12, laser cut without the connector links 13, are mounted onto the mandrel 36 to form a mandrel assembly 38 (FIG. 7B) with the rings spaced an equal distance apart from each other. The distance between the cylindrical stent rings 12, however, can be set further apart in order to increase stent flexibility. The mandrel assembly 38 with the cylindrical stent rings 12 thereon is dipped into the polymer solution. As depicted in FIG. 7C, the coated cylindrical rings 42 become embedded into the polymer material 44 as a result of the dip-coating process. After dipping the mandrel assembly 38 into the polymer solution, the polymer cures thereon. The dip-coating of the mandrel assembly 38 in the polymer solution is repeated until a desired thickness of the stent is achieved. The struts of the cylindrical stent rings 12 typically have a thickness in the range of about 25 microns to 350 microns. Preferably, the consecutive layers of polymer material coating the cylindrical stent rings 12 have a thickness in the range of about 25 microns to 200 microns. Upon satisfaction of the relative thickness of the dip-coated mandrel assembly 38, the newly fabricated dip-coated stent 40 (FIG. 7C) is removed from the mandrel 36 and the ends of the stent can be trimmed. If a dip-coated stent 40 having side branch access is desired, a perforated pattern can be cut into the polymer material (not shown) to produce the final configuration.

A lumenal surface (i.e., the inner surface area of the rings in contact with bloodflow) of the polymer coated rings 42 from the dip-coated covered stent 40 can be optionally coated asymmetrically with an anticoagulant such as heparin, IIb/IIIa inhibitor, PEG, or hyaluronic acid.

Exemplary of the metallic material forming the cylindrical stent rings 12 includes stainless steel, titanium, nickel titanium, tantalum, gold, cobalt-chromium, platinum, palladium, and iradium. If a deformable metal, such as stainless steel, is used for the cylindrical stent ring material, then a high strength plastic polymer, such as polyetheretherketone (PEEK), and polyimide (e.g., Ultem® by GE Plastics), is used to prevent excessive recoil of the dip-coated stent after expansion. Further, if a self-expanding superelastic material, such as nickel-titanium (nitinol), is used for the stent rings, then a high strength elastic polymer, such as shape memory polymers that have two component polymers (e.g., oligo (e-caprolactone) dimethacrylate) and co-monomers (e.g., n-butyl acrylate), modified polycyclooctene, and segmented polyurethanes with low molecular weight, is used as the dip-coating of the stent. Exemplary of other materials from which the cylindrical rings are formed include liquid crystalline, and liquid crystallin blends with other polymers, ceramics, and ceramic-reinforced polymers.

Exemplary of the biocompatible polymer material forming the entire covering of the dip-coated stent 40 includes the group of polymers consisting of polyurethanes, polyetherurethanes, polyesterurethanes, silicone, thermoplastic elastomer, sulfonated A-BA-type tri-block polymer, polyether-amide thermoplastic elastomer, fluoroelastomers, polyvinyledenefluoride (PVDF) and copolymers of PVDF, fluorosilicone elastomer, styrene-butadiene-styrene rubber, styrene-isoprene-styrene rubber, polybutadiene, polyisoprene, neoprene (polychloroprene), ethylene-propylene elastomer, chlorosulfonated polyethylene elastomer, butyl rubber, polysulfide elastomer, polyacrylate elastomer, nitrile, rubber, a family of elastomers composed of styrene, ethylene, propylene, aliphatic polycarbonate polyurethane, polymers augmented with antioxidants, bioactive polymers augmented with image enhancing materials, ceramics, polymers having a proton (H+) core, polymers augmented with protons (H+), polyester copolymer elastomers, biodegradable polymers, polyethylene, polycaprolactone, PLLA, PLA, PGA, PLGA, polyanhydrids, polyphothazenes, polyorthoesters, Elasteon® (manufactured by Aortech Corp., located in England), chitosin alginate, collagen, and elastin.

Figure 8:
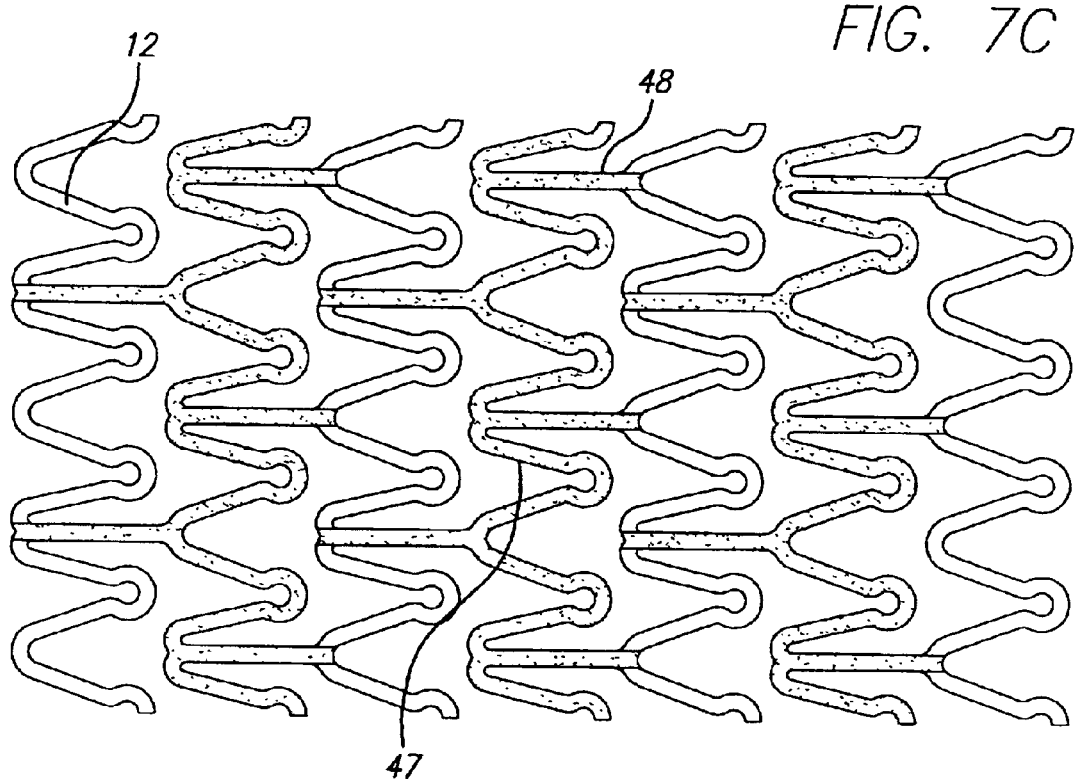
FIG. 8 is a plan view of a flattened section of a hybrid stent illustrating an alternating pattern of metallic rings and polymer rings and links.

Referring to FIG. 8, a flattened section of a hybrid stent having an alternating pattern of metallic rings 12 and polymer rings 47 and links 48 is shown. A method of fabricating this type of hybrid stent involves positioning a plurality of cylindrical stent rings 12 laser cut without connector links 13 into an injection molding apparatus consisting of a mandrel 110 having stent-patterned ring grooves 111. The cylindrical stent rings 12 are positioned at every other section of stent-patterned ring grooves 111 in the injection molding apparatus so that there is an open channel of stent-patterned ring grooves 111 and connector links 112 in between each section for the injection of polymer material to form the polymer cylindrical rings 47 and polymer links 48. The mandrel 110 is encased within a plurality of outer mold covers 115 that lock in place, such as by clamping. The outer mold covers 115 have a mirror image of the groove stent pattern that correspond to the grooves in the mandrel. FIGS. 13–17 describe in further detail the injection molding apparatus for forming the polymer cylindrical stent rings and links. The alternating pattern of metallic rings 12 and polymer rings 47 and links 48 is not limited to equal frequency. For example, the metal-polymer pattern ("m-p-m-p- . . . ") may be m-p-p-m- . . . or m-m-p-m-m- . . . or any configuration so long as the radial strength and other desirable attributes (i.e., flexibility) are maintained. Following the cool down of the injection molding apparatus and the solidification of the polymer, the outer mold covers 115 (FIGS. 13–17) are removed from the mandrel 110 and any excess polymer material can be removed by known means.

Figure 9:
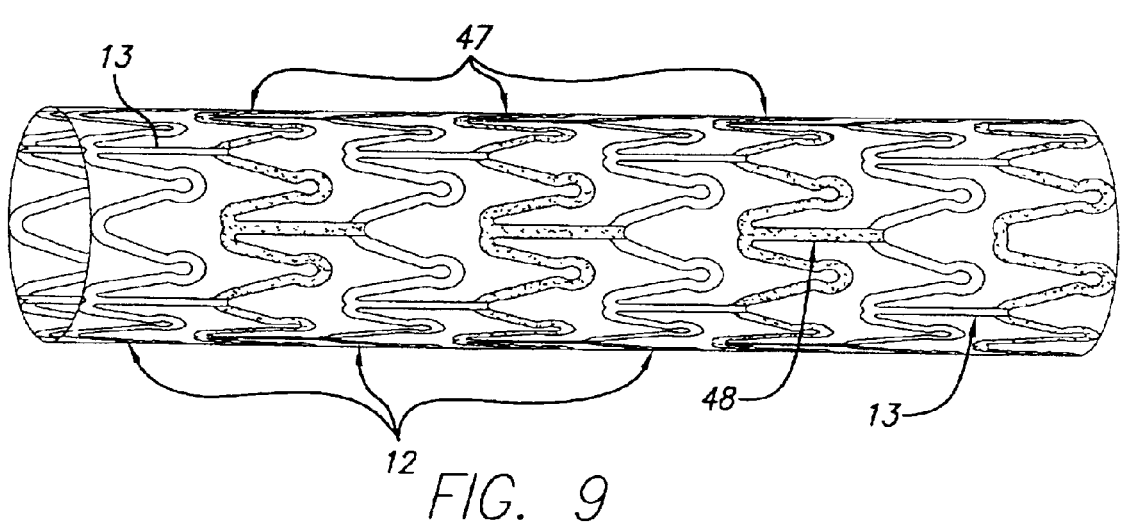
FIG. 9 is a perspective view of a hybrid stent of the invention having alternating rings and links formed of metallic materials and polymer materials.

FIG. 9 illustrates a hybrid stent having alternating rings and links formed of metallic materials and polymer materials. One method of making this type of hybrid stent involves placing a plurality of cylindrical stent rings 12 laser cut with alternating connector links 13 on each section of the rings into an injection molding apparatus consisting of a mandrel 110 having stent-patterned ring grooves 111 and connector link channels 112. Specifically, the metallic connector links 13 are laser cut with the cylindrical stent rings 12 in such a pattern so that one side of the section of cylindrical stent rings is formed of metallic links that alternate with the links 48 formed of a polymer material on the other side. The mandrel 110 is encased within a plurality of outer mold covers 115 that lock in place, such as by clamping. The outer mold covers 115 have a mirror image of the groove stent pattern that correspond to the grooves in the mandrel. FIGS. 13–17 describe in further detail the injection molding apparatus for forming the cylindrical rings and links with the injection of a biocompatible polymer material into select grooves of the apparatus.

Again, after the cooling down of the outer mold covers 115 and the mandrel 110, the polymer solidifies, the outer mold covers are released from the mandrel, and the cylindrical rings are then removed from the mandrel along with the links so that a completed stent with the rings attached to each other is formed. The completed hybrid stent consists of alternating metallic rings 12 and links 13, and polymer rings 47 and links 48. The alternating pattern of metallic and polymer rings 12 and 47 is not limited to equal frequency. For example, the metal-polymer pattern ("m-p-m-p- . . . ") may be m-p-p-m- . . . or m-m-p-m-m- . . . or any configuration so long as the radial strength and other desirable attributes (i.e., flexibility) are maintained.

Exemplary of the metallic material used in forming the alternating rings and links of the hybrid stent in FIGS. 8–9 includes stainless steel, titanium, nickel titanium, tantalum, gold, cobalt-chromium, platinum, palladium, and iradium.

Exemplary of the biocompatible polymer material used in the injection molding apparatus for forming the alternating polymer rings and links in FIGS. 8–9 includes the group of polymers consisting of polyurethanes, polyetherurethanes, polyesterurethanes, silicone, thermoplastic elastomer, sulfonated A-BA-type tri-block polymer, polyether-amide thermoplastic elastomer, fluoroelastomers, polyvinyledenefluoride (PVDF) and copolymers of PVDF, fluorosilicone elastomer, styrene-butadiene-styrene rubber, styrene-isoprene-styrene rubber, polybutadiene, polyisoprene, neoprene (polychloroprene), ethylene-propylene elastomer, chlorosulfonated polyethylene elastomer, butyl rubber, polysulfide elastomer, polyacrylate elastomer, nitrile, rubber, a family of elastomers composed of styrene, ethylene, propylene, aliphatic polycarbonate polyurethane, polymers augmented with antioxidants, bioactive polymers augmented with image enhancing materials, ceramics, polymers having a proton (H+) core, polymers augmented with protons (H+), polyester copolymer elastomers, biodegradable polymers, polyethylene, polycaprolactone, PLLA, PLA, PGA, PLGA, polyanhydrids, polyphothazenes, polyorthoesters, Elasteon® (manufactured by Aortech Corp., located in England), chitosin alginate, collagen, and elastin.

With further reference to FIGS. 8–9, the polymer rings 47 of the stent can be made porous for the incorporation of drugs (i.e., anticoagulants) therein and the eventual release within the body lumen at the treatment site while in the implanted diameter configuration. The porosity of the polymer rings 47 can either be pre-generated with the drug loaded prior to implantation of the stent or generated during implantation of the stent. Exemplary of various materials that can be used to generate pores in the polymer coating include PEG, salts (i.e., NaCl), L-arginine, and poragen.

FIG. 10 illustrates an alternative embodiment of a linkless hybrid stent 24 having adjacent cylindrical stent rings attached to each other by known means, such as by welding. In this particular embodiment, each of the peaks of the adjacent cylindrical rings 12 and 46 form a weld point 50 throughout the longitudinal axis of the stent 22. A method of fabricating the linkless hybrid stent 24 includes positioning a plurality of metallic cylindrical stent rings 12, laser cut without the connector links 13, in an injection molding apparatus. An alternative injection molding apparatus (not shown) can be used that includes stent-patterned grooves without the connector channels in order to form the alternating polymer cylindrical rings 46. The laser cut cylindrical rings 12 are positioned in a manner which allows for an open channel of the stent-patterned grooves to be in between each section of the metallic cylindrical rings. The polymer material is injected into the open channels of the injection molding apparatus in the same manner as for the standard injection molding apparatus in forming the polymer cylindrical rings 46 as shown in FIGS. 13–17. After the apparatus has cooled down and the polymer material has solidified, the outer mold covers 115 (FIGS. 13–17) are removed from the mandrel 110 and any excess polymer material can be removed by known means. The cylindrical stent rings 12 and the polymer stent rings 46 can be directly attached to each other through various known means, such as welding, which occurs after the formation of the linkless hybrid stent.

FIG. 11 illustrates an alternative embodiment of the present invention in which the alternating polymer rings 46 can be selectively placed at the stent ends to prevent vessel wall injury at the edges of the stent.

As shown in FIG. 12A, in an alternative embodiment of the present invention, a laminated linkless polymer stent can be fabricated from polymer tubing thereby eliminating the use of metallic links. The replacement of metallic links with more flexible polymer tubing that connects the rings enables the stent to accommodate a larger number of rings, resulting in significant radial strength without any compromise in flexibility of the stent. Also, the presence of the polymer tube will provide support to a much larger portion of the arterial wall, thereby increasing stent scaffolding. In traditional stents, the struts push against the lumen causing highly localized concentrated stresses. These stresses can cause rupture of the fibrous caps in a fibroatheroma. However, in the case of the linkless polymer stent described here, a much larger surface area apposes the lumen. Therefore, the stresses induced in the lumen by the stent are lower.

A method of fabricating the laminated linkless polymer stent includes mounting a first polymer tube 52 on a mandrel 36 followed by placing a plurality of flexible, cylindrical stent rings 12 onto the first polymer tube, as shown in FIG. 12B. A second polymer tube 54 wraps around the entire surface area of the first polymer tube 52 with the rings inserted thereon. The wall thickness of the first polymer tube 52 and second polymer tube 54 is approximately 0.002 to 0.003 inches. The lamination of the metallic rings 12 between the two polymer tubes 52 and 54 consists of placing a shrink tubing 56 over the second polymer tube 54 and applying heat and pressure, known as laser bonding, in order to shrink the tubing. As a result of being exposed to the laser beam, the shrink tubing 56 contracts and applies a pressure on the second polymer tube causing it to press against the stent struts 26 and the first polymer tube 52. The heat from the laser beam causes the first polymer tube 52 and second polymer tube 54 to melt and fuse together into one polymer tube 58. The amount of time that the laser is applied to the shrink tubing 56 varies depending on the length of the polymer tubing. For example, polymer tubing that is shorter in length requires only a quick application of the laser, such as a few seconds, whereas polymer tubing that is longer in length requires a longer application of the laser in order to be effective, such as a minute. One type of laser that can be used in accordance with the invention is an Excimer (manufactured by Lambda Physik USA, Inc., located in Fort Lauderdale, Fla., and Polytech P.I., located in Boston, Mass.). Following application of heat and pressure to the shrink tubing 56, the shrink tubing and the mandrel 36 is removed from the newly formed laminated linkless polymer stent.

As an alternative to laser bonding the polymer tubes together, the laminated, linkless polymer stent 60 can be produced using the technique of blow molding. This process involves the simultaneous application of heat and pressure to the inner surface of the first polymer tube 52 and the outer surface of the second polymer tube 54. In blow molding the specific areas of the first polymer tube 52 and second polymer tube 54, the polymer material is forced to flow and hence laminate the metallic stent rings 12. The heat that is applied simultaneously with the pressure to the specified surfaces of the first polymer tube 52 and the second polymer tube 54 during the blow molding procedure has a temperature that is higher than the melting point of the polymer material. The approximate pressure that can be applied to the specified areas of the first polymer tube 52 and the second polymer tube 54 ranges from 20 to 500 psi for about 10 to 60 seconds.

Exemplary of the metallic material used for the cylindrical stent rings in FIGS. 12A–B includes stainless steel, titanium, nickel titanium, tantalum, gold, cobalt-chromium, platinum, palladium, and iradium. Because the links are incorporated in the polymer, there is a greater flexibility in the choice of metals that can be used for the stent rings. The radiopacity of the stent can be increased by using metals such as gold, paladium, platinum, and iradium, as listed above. Further, the stent can be made MRI compatible by substituting gold or silver for stainless steel.

Exemplary of the polymer tubing used in fabricating the laminated, linkless polymer stent includes the group of polymers consisting of polyurethanes, polyetherurethanes, polyesterurethanes, silicone, thermoplastic elastomer, sulfonated A-BA-type tri-block polymer, polyether-amide thermoplastic elastomer, fluoroelastomers, polyvinyledenefluoride (PVDF) and copolymers of PVDF, fluorosilicone elastomer, styrene-butadiene-styrene rubber, styrene-isoprene-styrene rubber, polybutadiene, polyisoprene, neoprene (polychloroprene), ethylene-propylene elastomer, chlorosulfonated polyethylene elastomer, butyl rubber, polysulfide elastomer, polyacrylate elastomer, nitrile, rubber, a family of elastomers composed of styrene, ethylene, propylene, aliphatic polycarbonate polyurethane, polymers augmented with antioxidants, bioactive polymers augmented with image enhancing materials, ceramics, polymers having a proton (H+) core, polymers augmented with protons (H+), polyester copolymer elastomers, biodegradable polymers, polyethylene, polycaprolactone, polyester polycaprolactone copolymers, PLLA, PLA, PGA, PLGA, polyanhydrids, polyphothazenes, polyorthoesters, Elasteon® (manufactured by Aortech Corp., located in England), chitosin alginate, collagen, and elastin.

Each of the various types of stents described above, including the dip-coated stent 40 (FIGS. 7A–C), the hybrid stents (FIGS. 8–11) with alternating rings and links of metallic and polymer materials, and the laminated linkless polymer stent (FIGS. 12A–B) may be further enhanced with the incorporation of drugs into the polymer coating to be eluted therefrom in the treatment of disease. Exemplary of various types of drugs that can be incorporated within the polymer coating include antiplatelets, anticoagulants, antifibrins, antithrombins, and antiproliferatives. In this embodiment, the metallic cylindrical stent rings consist of three layers of various materials coated thereon. The three layers of the metallic rings include a primer coat covering the outer surface of the rings, a middle polymer layer with the drug incorporated therein or solely the drug without the polymer, and a top coat layer. The thickness of all three layers combined ranges from 3 microns to 300 microns. The primer coat has a thickness of about 0.5 microns to 50 microns. The middle layer incorporating the drug therein or solely the drug without the polymer has a thickness of about 2 microns to 150 microns. The non-metallic polymer rings consist of the drug incorporated therein the polymer material and a top coat layer thereon. The top coat layer has a thickness of about 0.5 microns to 100 microns. The top coat layer helps to control the release of the drug into the body. However, a top coat layer may not be necessary if the primer coat and the middle layer provide the desired pharmacokinetics for therapeutic benefit.

Figure 14:
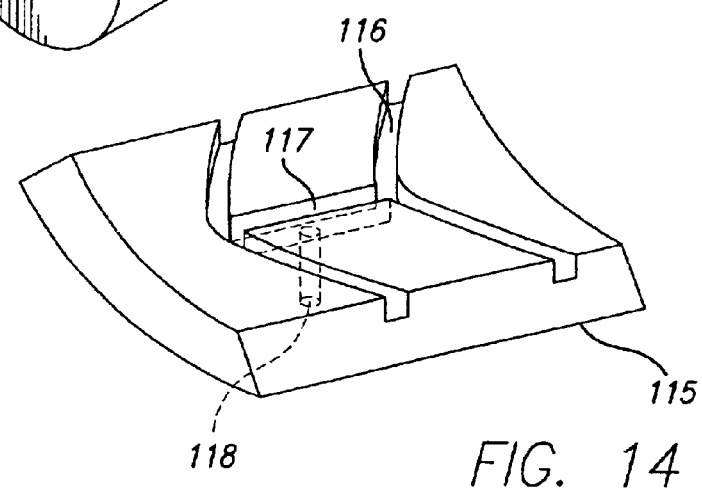
FIG. 14 is a perspective view of a quarter arc section of an outer mold cover having grooves for the cylindrical rings and links.
Figure 15:
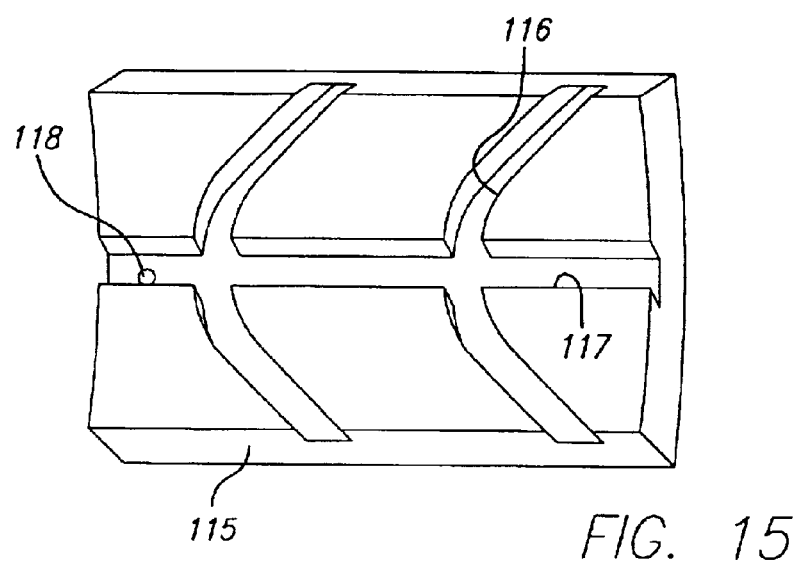
FIG. 15 is a perspective view of a quarter arc section of the outer mold cover having grooves for the cylindrical rings and links.
Figure 16:
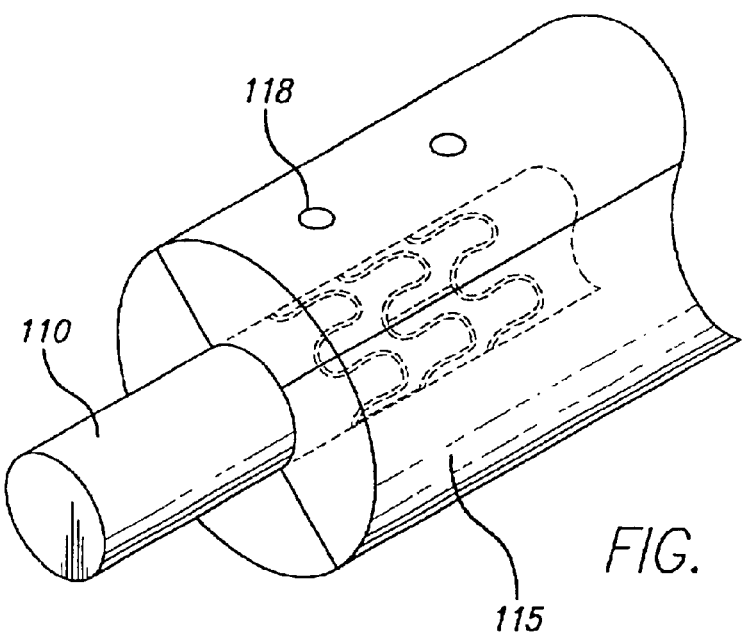
FIG. 16 is a partial perspective view of the mandrel with the quarter arc section outer mold covers positioned over the mandrel for use in the injection molding process.
Figure 17:
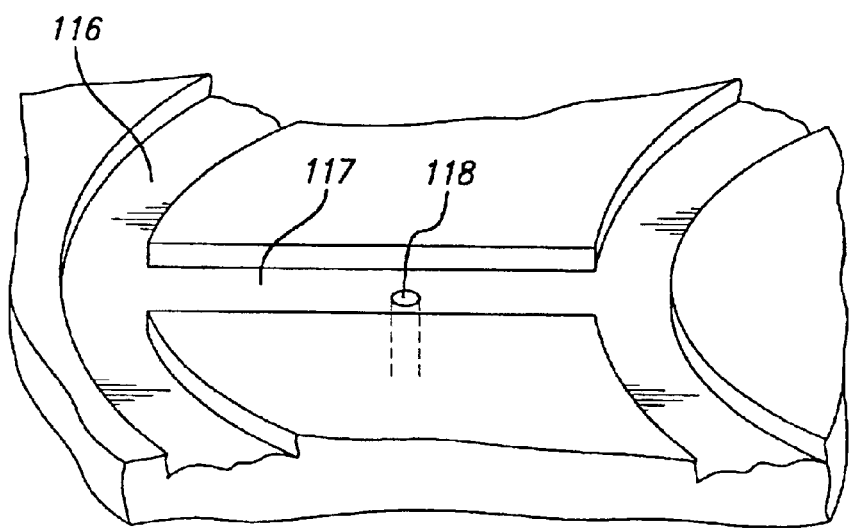
FIG. 17 is a partial elevational view of a portion of an outer mold cover depicting the gate through which the polymer is injected to form the links.

In keeping with one method of the invention for forming the links and attaching them to the cylindrical rings, an injection molding apparatus is shown in FIGS. 13–17. A mandrel 110 is provided with grooves that correspond to the pattern of the cylindrical rings 12. The cylindrical rings are placed over the mandrel and fitted into the ring grooves 111. The mandrel also has link grooves 112 in which the injected polymer will flow in order to attach one cylindrical ring to an adjacent cylindrical ring. After the cylindrical rings are fitted into the ring grooves 111, and as shown in FIG. 14, a plurality of outer mold covers 115 are fitted around the mandrel and locked in place by known means, such as by clamping. The outer mold covers 115 typically are in cylindrical sections as depicted in FIGS. 14–17 and it is preferred that from two to four arc sections of outer mold covers be used to encase the mandrel 110. Each of the outer mold covers has grooves that correspond to grooves in the mandrel. Specifically, the outer mold covers have ring grooves 116 and link grooves 117 that correspond to the ring grooves 111 and link grooves 112 of the mandrel 110. The polymer used to form the links is injected by known techniques through gates 118 located at multiple positions along the outer mold covers. The gates provide openings or apertures through the outer mold covers to correspond to the location of the link grooves 112,117 so that as the polymer is injected through the outer mold cover, it will flow into the link groove 112,117 and form the link pattern.

After the outer mold covers and mandrel have a chance to cool so that the polymer solidifies, the outer mold covers 115 can be removed from the mandrel 110 and any excess flashing from the gates 118 can be removed by known means. The cylindrical rings 12 are then removed from the mandrel along with the links so that a completed stent with the rings attached to each other are formed.

Figure 18:
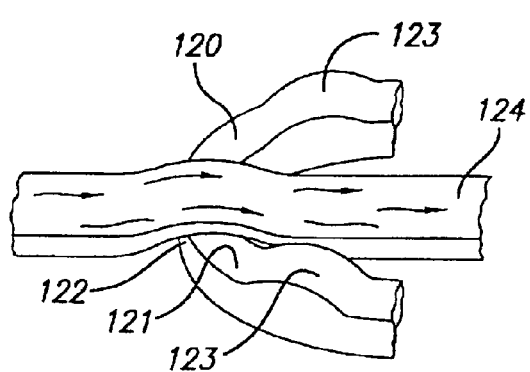
FIG. 18 is a partial elevational view of a section of a cylindrical ring having a thin and thick portion and a polymer link encapsulating the apex portion of the ring.

In an alternative embodiment, as shown in FIG. 18, the same mandrel 110 and outer mold covers 115 can be used to form polymer links to attach cylindrical rings that add varying degrees of thickness along portions of the cylindrical ring. For example, as shown in FIG. 18, a U-shaped portion 120 has a thinner portion 121 at the apex 122 and thicker portion 123 as you move away from the apex. In this configuration, once the cylindrical ring is mounted onto the mandrel, the outer mold covers 115 will require ring grooves 116 that correspond to the thinner and thicker portions 121,123 of the rings. Thereafter, the polymer injection process previously described to form the links is used to form link 124 which flows over the thinner portion 121 to connect one cylindrical ring to an adjacent cylindrical ring. In this embodiment, the polymer link 124 will encompass or flow around the U-shaped portion 120 at the apex 122 to form the attachment of the link to the cylindrical ring. Again, after the assembly has cooled and the polymer has solidified, the outer mold covers are removed and the stent is removed from the mandrel. Any excess polymer or flash can be removed by known methods.

With respect to the foregoing description of the polymer injection process, it is desirable that the cylindrical rings be placed on the mandrel 110 while the rings are in a somewhat expanded configuration. It is possible, however, to perform the injection mold process when the rings are in an unexpanded configuration on the mandrel, but it is easier in the expanded condition.

With respect to all of the aforedescribed embodiments in which polymer links are used to connect adjacent rings, one or more metal links may be required between adjacent rings to provide better relative orientation between the rings. Also, the metal links will provide more structural support during delivery and after the stent has been expanded and implanted in the artery or other vessel. Thus, it is in keeping with the invention that both polymer links and metal links may be used in any of the stent embodiments disclosed without departing from the invention.

One method of making the stent 10 of the invention is to first laser cut the cylindrical rings 12 from a tube so that the rings are not connected by the aforedescribed polymer links 13. The rings are then placed on a mandrel into stent-patterned grooves and encased with a locking sleeve having a mirror of the stent pattern cut into its inner surface. The only exposed region of the stent is the channels that correspond to the links that will connect the rings. The mandrel and the encapsulating sleeve permit the injection of a polymer which fills the channels corresponding to the links. The polymer is used to form the links which connect adjacent rings. The stent forming processes are described in more detail with the description of the formation of the stent cylindrical rings 12 by a laser cutting process.

The aforedescribed illustrative stent 10 and similar stent structures can be made in many ways. One method of making the stent rings 12 is to cut a thin-walled tubular member, such as stainless steel tubing to remove portions of the tubing in the desired pattern for the stent, leaving relatively untouched the portions of the metallic tubing which are to form the rings.

The tubing may be made of suitable biocompatible material such as stainless steel, cobalt-chromium (CoCn, NP35N), titanium, nickel-titanium (NiTi), and similar alloys. The stainless steel tube may be Alloy type: 316L SS, Special Chemistry per ASTM F138-92 or ASTM F139-92 grade 2. Special Chemistry of type 316L per ASTM F138-92 or ASTM F139-92 Stainless Steel for Surgical Implants in weight percent.

| | |
|---|---|
| Carbon (C) | 0.03% max. |
| Manganese (Mn) | 2.00% max. |
| Phosphorous (P) | 0.025% max. |
| Sulphur (S) | 0.010% max. |
| Silicon (Si) | 0.75% max. |
| Chromium (Cr) | 17.00–19.00% |
| Nickel (Ni) | 13.00–15.50% |
| Molybdenum (Mo) | 2.00–3.00% |
| Nitrogen (N) | 0.10% max. |
| Copper (Cu) | 0.50% max. |
| Iron (Fe) | Balance |

The stent diameter is very small, so the tubing from which it is made must necessarily also have a small diameter. Typically the stent has an outer diameter on the order of about 0.06 inch in the unexpanded condition, the same outer diameter of the tubing from which it is made, and can be expanded to an outer diameter of 0.1 inch or more. The wall thickness of the tubing is about 0.003 inch.

The tubing is put in a rotatable collet fixture of a machine-controlled apparatus for positioning the tubing relative to a laser. According to machine-encoded instructions, the tubing is rotated and moved longitudinally relative to the laser which is also machine-controlled. The laser selectively removes the material from the tubing by ablation and a pattern is cut into the tube. The tube is therefore cut into the discrete pattern of the finished cylindrical rings.

Cutting a fine structure (0.0035 inch web width) requires minimal heat input and the ability to manipulate the tube with precision. It is also necessary to support the tube yet not allow the stent structure to distort during the cutting operation. In one embodiment, the tubes are made of stainless steel with an outside diameter of 0.060 inch to 0.095 inch and a wall thickness of 0.002 inch to 0.004 inch. These tubes are fixtured under a laser and positioned utilizing a CNC to generate a very intricate and precise pattern. Due to the thin wall and the small geometry of the stent pattern (0.0035 inch typical strut or ring width), it is necessary to have very precise control of the laser, its power level, the focused spot size, and the precise positioning of the laser cutting path.

In order to minimize the heat input into the stent structure, which prevents thermal distortion, uncontrolled burn out of the metal, and metallurgical damage due to excessive heat, and thereby produce a smooth debris free cut, a Q-switched Nd/YAG, typically available from Quantronix of Hauppauge, N.Y., that is frequency doubled to produce a green beam at 532 nanometers is utilized. Q-switching produces very short pulses (<100 nS) of high peak powers (kilowatts), low energy per pulse ($\leq 3$ mJ), at high pulse rates (up to 40 kHz). The frequency doubling of the beam from 1.06 microns to 0.532 microns allows the beam to be focused to a spot size that is 2 times smaller, therefore increasing the power density by a factor of 4 times. With all of these parameters, it is possible to make smooth, narrow cuts in the stainless tubes in very fine geometries without damaging the narrow struts that make up to stent structure.

Hence, the system makes it possible to adjust the laser parameters to cut narrow kerf width which will minimize the heat input into the material.

The positioning of the tubular structure requires the use of precision CNC equipment such as that manufactured and sold by Anorad Corporation. In addition, a unique rotary mechanism has been provided that allows the computer program to be written as if the pattern were being cut from a flat sheet. This allows both circular and linear interpolation to be utilized in programming. Since the finished structure of the stent is very small, a precision drive mechanism is required that supports and drives both ends of the tubular structure as it is cut. Since both ends are driven, they must be aligned and precisely synchronized, otherwise the stent structure would twist and distort as it is being cut.

The optical system which expands the original laser beam, delivers the beam through a viewing head and focuses the beam onto the surface of the tube, incorporates a coaxial gas jet and nozzle that helps to remove debris from the kerf and cools the region where the beam interacts with the material as the beam cuts and vaporizes the metal. It is also necessary to block the beam as it cuts through the top surface of the tube and prevent the beam, along with the molten metal and debris from the cut, from impinging on the opposite surface of the tube.

In addition to the laser and the CNC positioning equipment, the optical delivery system includes a beam expander to increase the laser beam diameter, a circular polarizer, typically in the form of a quarter wave plate, to eliminate polarization effects in metal cutting, provisions for a spatial filter, a binocular viewing head and focusing lens, and a coaxial gas jet that provides for the introduction of a gas stream that surrounds the focused beam and is directed along the beam axis. The coaxial gas jet nozzle (0.018 inch I.D.) is centered around the focused beam with approximately 0.010 inch between the tip of the nozzle and the tubing. The jet is pressurized with oxygen at 20 psi and is directed at the tube with the focused laser beam exiting the tip of the nozzle (0.018 inch dia.) The oxygen reacts with the metal to assist in the cutting process very similar to oxyacetylene cutting. The focused laser beam acts as an ignition source and controls the reaction of the oxygen with the metal. In this manner, it is possible to cut the material with a very fine kerf with precision. In order to prevent burning by the beam and/or molten slag on the far wall of the tube I.D., a stainless steel mandrel (approx. 0.034 inch dia.) is placed inside the tube and is allowed to roll on the bottom of the tube as the pattern is cut. This acts as a beam/debris block protecting the far wall I.D.

Alternatively, this may be accomplished by inserting a second tube inside the ring tubing which has an opening to trap the excess beam energy that is transmitted through the kerf. This second tubing also collects the debris that is ejected from the laser cut kerf. A vacuum or positive pressure can be placed in this shielding tube to remove the collected debris.

Another technique that could be utilized to remove the debris from the kerf and cool the surrounding material would be to use the inner beam blocking tube as an internal gas jet. By sealing one end of the tube and making a small hole in the side and placing it directly under the focused laser beam, gas pressure could be applied creating a small jet that would force the debris out of the laser cut kerf from the inside out. This would eliminate any debris from forming or collecting on the inside of the stent structure. It would place all the debris on the outside. With the use of special protective coatings, the resultant debris can be easily removed.

In most cases, the gas utilized in the jets may be reactive or non-reactive (inert). In the case of reactive gas, oxygen or compressed air is used. Compressed air is used in this application since it offers more control of the material removed and reduces the thermal effects of the material itself. Inert gas such as argon, helium, or nitrogen can be used to eliminate any oxidation of the cut material. The result is a cut edge with no oxidation, but there is usually a tail of molten material that collects along the exit side of the gas jet that must be mechanically or chemically removed after the cutting operation.

The cutting process utilizing oxygen with the finely focused green beam results in a very narrow kerf (approx. 0.0005 inch) with the molten slag re-solidifying along the cut. This traps the cut out scrap of the pattern requiring further processing. In order to remove the slag debris from the cut allowing the scrap to be removed from the remaining stent pattern, it is necessary to soak the cut tube in a solution of HCl for approximately 8 minutes at a temperature of approximately 55° C. Before it is soaked, the tube is placed in a bath of alcohol/water solution and ultrasonically cleaned for approximately 1 minute to remove the loose debris left from the cutting operation. After soaking, the tube is then ultrasonically cleaned in the heated HCl for 1–4 minutes depending upon the wall thickness. To prevent cracking/breaking of the struts attached to the material left at the two ends of the stent pattern due to harmonic oscillations induced by the ultrasonic cleaner, a mandrel is placed down the center of the tube during the cleaning/scrap removal process. At completion of this process, the stent structures are rinsed in water. They are now ready for electropolishing.

The stent rings are preferably electrochemically polished in an acidic aqueous solution such as a solution of ELECTRO-GLO #300, sold by the ELECTRO-GLO Co., Inc. in Chicago, Ill., which is a mixture of sulfuric acid, carboxylic acids, phosphates, corrosion inhibitors and a biodegradable surface active agent. The bath temperature is maintained at about 110–135° F. and the current density is about 0.4 to about 1.5 amps per in.$^2$. Cathode to anode area should be at least about two to one.

Direct laser cutting produces edges which are essentially perpendicular to the axis of the laser cutting beam, in contrast with chemical etching and the like which produce pattern edges which are angled. Hence, the laser cutting process essentially provides strut cross-sections, from cut-to-cut, which are square or rectangular, rather than trapezoidal.

The foregoing laser cutting process to form the cylindrical rings 12 can be used with other metals including cobalt-chromium, titanium, tantalum, nickel-titanium, gold, iradium, platinum, palladium, and other biocompatible metals suitable for use in humans, and typically used for intravascular stents. Further, while the formation of the cylindrical rings is described in detail, other processes of forming the rings are possible and are known in the art, such as by using chemical etching, electronic discharge machining, stamping, and other processes.

Generally speaking, cylindrical rings 12 and links 13 can be formed by injection molding pursuant to the methods described herein.

While the invention has been described in connection with certain disclosed embodiments, it is not intended to limit the scope of the invention to the particular forms set forth, but, on the contrary it is intended to cover all such alternatives, modifications, and equivalents as may be included in the spirit and scope of the invention as defined by the appended claims.

What is claimed:

1. A method of making a dip-coated covered stent for use in a body lumen, comprising:

providing a mandrel coated with a biocompatible polymer to form a base coat layer thereon;

providing a plurality of cylindrical stent rings, each of the rings being expandable in a radial direction, each of the rings having a first delivery diameter, and a second implanted diameter, aligned on a common longitudinal axis;

mounting the plurality of cylindrical stent rings onto the mandrel to form a mandrel assembly wherein the rings are spaced an equal distance apart from each other;

depositing the mandrel assembly in a polymer solution to form a dip-coated covered stent such that the rings are fully covered including all surfaces facing said longitudinal axis and all surfaces facing away from said longitudinal axis; and removing the dip-coated covered stent from the mandrel.

2. The method of claim 1, wherein the mandrel is formed of a material from the group consisting of teflon (PTFE), nylon, polyimide, polyethylene, and PET.

3. The method of claim 1, wherein the polymer solution cures to form the base coat layer of the mandrel prior to mounting the cylindrical rings thereon.

4. The method of claim 1, wherein the cylindrical rings are formed from a metallic material taken from the group of materials consisting of stainless steel, titanium, nickel titanium, tantalum, gold, cobalt-chromium, platinum, palladium, and iradium.

5. The method of claim 1, wherein the cylindrical rings are formed from a material taken from the group consisting of liquid crystallin, and liquid crystallin blends with other polymers, ceramics, and ceramic-reinforced polymers.

6. The method of claim 1, wherein flexibility of the stent increases when the distance between the cylindrical rings increases.

7. The method of claim 1, wherein the mandrel assembly is deposited in the polymer solution by dip-coating.

8. The method of claim 1, wherein the biocompatible polymer covering the cylindrical rings is taken from the group of polymers consisting of polyurethanes, polyetherurethanes, polyesterurethanes, silicone, thermoplastic elastomer, sulfonated A-BA-type tri-block polymer, polyether-amide thermoplastic elastomer, fluoroelastomers, polyvinyledenefluoride (PVDF) and copolymers of PVDF, fluorosilicone elastomer, styrene-butadiene-styrene rubber, styrene-isoprene-styrene rubber, polybutadiene, polyisoprene, neoprene (polychloroprene), ethylene-propylene elastomer, chlorosulfonated polyethylene elastomer, butyl rubber, polysulfide elastomer, polyacrylate elastomer, nitrile, rubber, a family of elastomers composed of styrene, ethylene, propylene, aliphatic polycarbonate polyurethane, polymers augmented with antioxidants, bioactive polymers augmented with image enhancing materials, ceramics, polymers having a proton (H+) core, polymers augmented with protons (H+), polyester copolymer elastomers, biodegradable polymers, polyethylene, polycaprolactone, PLLA, PLA, PGA, PLGA, polyanhydrids, polyphothazenes, polyorthoesters, Elasteon®, chitosin alginate, collagen, and elastin.

9. The method of claim 1, wherein prior to mounting the cylindrical rings on the polymer coated mandrel, the polymer is cured on the mandrel assembly.

10. The method of claim 1, wherein the method of dip-coating the mandrel assembly in the polymer solution is repeated until the polymer covering the cylindrical rings attains a thickness of about 25 microns to 200 microns.

11. The method of claim 1, wherein the cylindrical rings have a thickness of about 25 microns to 350 microns.

12. The method of claim 1, wherein each end of the dip-coated covered stent is trimmed.

13. The method of claim 1, wherein a perforated pattern is cut into the dip-coated covered stent.

14. The method of claim 1, wherein a drug is incorporated within the layer of the biocompatible polymer coating the cylindrical rings.

15. The method of claim 14, wherein the drug includes antiplatelets, anticoagulants, antifibrins, antithrombins, and antiproliferatives.

16. The method of claim 14, wherein the cylindrical rings consist of three layers, including a primer coat, a middle layer of the polymer with the drug incorporated therein, and a top coat.

17. The method of claim 16, wherein the three layers combined have a thickness of about 3 microns to 300 microns.

18. The method of claim 16, wherein the middle layer of the polymer with the drug incorporated therein has a thickness of about 2 microns to 150 microns.

19. The method of claim 1, wherein a lumenal side of the rings are asymmetrically coated.

20. The method of claim 1, wherein the lumenal side of the rings are asymmetrically coated with at least one of heparin, IIb/IIIa inhibitors, PEG, and hyaluronic acid.

21. The method of claim 1, wherein all of said cylindrical stent rings are exclusively linked by said polymer.

22. The method of claim 1, wherein said polymer is exclusively relied upon to link said cylindrical stent rings to one another.

23. The method of claim 1, wherein only said polymer forms links between any of said cylindrical stent rings.

* * * * *